United States Patent
Chon et al.

(10) Patent No.: US 11,903,573 B2
(45) Date of Patent: Feb. 20, 2024

(54) TROCAR-CANNULA ASSEMBLY CAP

(71) Applicant: Alcon Inc., Fribourg (CH)

(72) Inventors: James Y. Chon, Irvine, CA (US); Joel Cicchella, Tustin, CA (US); Russell Finlay, Keller, TX (US); Grace Chuang Liao, Irvine, CA (US); Ashish Sinha, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/811,127

(22) Filed: Jul. 7, 2022

(65) Prior Publication Data

US 2023/0025096 A1 Jan. 26, 2023

Related U.S. Application Data

(60) Provisional application No. 63/223,682, filed on Jul. 20, 2021.

(51) Int. Cl.
*A61B 17/02* (2006.01)
*A61B 90/00* (2016.01)
*A61B 17/00* (2006.01)

(52) U.S. Cl.
CPC *A61B 17/0231* (2013.01); *A61B 2017/00424* (2013.01); *A61B 2017/00473* (2013.01); *A61B 2017/00858* (2013.01); *A61B 2017/00907* (2013.01); *A61B 2090/3904* (2016.02)

(58) Field of Classification Search
CPC ........ A61B 17/0231; A61B 2090/3904; A61B 2017/00424; A61B 2017/00473; A61B 2017/00858

USPC .............. 600/236, 398, 405, 406, 160, 178; 604/506, 263, 264, 164.08, 164.11
See application file for complete search history.

(56) References Cited

U.S. PATENT DOCUMENTS

| | | | |
|---|---|---|---|
| 4,880,017 A | 11/1989 | Soll et al. | |
| D457,955 S * | 5/2002 | Bilitz | ........................ D24/144 |
| 7,468,065 B2 | 12/2008 | Weber | |
| D612,052 S * | 3/2010 | McCollam | .................. D24/150 |
| 7,972,348 B1 | 7/2011 | Anderson | |
| 8,088,134 B2 | 1/2012 | Melki | |
| 9,968,372 B2 | 5/2018 | Chen et al. | |
| 2012/0158031 A1 | 6/2012 | Mccawley | |
| 2013/0102966 A1* | 4/2013 | Hanlon | .............. A61B 17/3421 604/164.11 |

(Continued)

FOREIGN PATENT DOCUMENTS

DE 102017206355 A1 10/2017

*Primary Examiner* — Eduardo C Robert
*Assistant Examiner* — David C Comstock

(57) ABSTRACT

A trocar-cannula insertion tool for ophthalmic procedures may include a cap with a body having a proximal end and a distal end opposite the proximal end. A marking element extends in a distal direction from the distal end of the body and includes at least one marking tip for forming one or more indentations on a patient's eye during an ophthalmic procedure. A manipulation element extends from the body in a direction different from the marking element and includes at least one manipulation tip for gripping a tissue of the patient's eye during the ophthalmic procedure. The cap may further include at least one window for exposing a photoluminescent cannula of the trocar-cannula insertion tool to light, enabling the cannula to absorb photons prior to insertion thereof.

15 Claims, 6 Drawing Sheets

(56) References Cited

U.S. PATENT DOCUMENTS

| | | | |
|---|---|---|---|
| 2015/0094751 A1* | 4/2015 | Chen .................. | A61B 17/3496 |
| | | | 606/185 |
| 2015/0201963 A1* | 7/2015 | Snow ................. | A61B 17/3421 |
| | | | 604/167.03 |
| 2021/0113780 A1* | 4/2021 | Parrag ................. | A61M 5/3148 |

* cited by examiner

TROCAR-CANNULA ASSEMBLY CAP

PRIORITY CLAIM

This application claims the benefit of priority of U.S. Provisional Patent Application Ser. No. 63/223,682 titled "TROCAR-CANNULA ASSEMBLY CAP," filed on Jul. 20, 2021, whose inventors are James Y. Chon, Joel Cicchella, Russell Finlay, Grace Chuang Liao and Ashish Sinha, which is hereby incorporated by reference in its entirety as though fully and completely set forth herein.

FIELD

The present disclosure relates to ophthalmic surgical tools, and more specifically, to trocar-cannula insertion tools and methods of use thereof.

BACKGROUND

Cannulas are one example of a microsurgical instrument used in ophthalmic surgical procedures, such as posterior segment surgical procedures. By way of example, cannulas may be used to aspirate fluids such as blood and aqueous humor from the interior ocular space, and aspirate and/or infuse fluids such as balanced salt solutions and silicone oils. These cannulas are typically connected to a vacuum or fluid source at a surgical control console by way of one or more flexible fluid lines.

During certain ophthalmic surgical procedures, a surgeon may further require several additional instruments throughout the procedure, such as a vitrectomy probe or laser probe, as well as an endoilluminator. This frequently requires that these instruments be repeatedly and/or sequentially inserted into and removed out of an incision site that provides access to the ocular space. To guard against trauma to the incision site from the repeated entry/exit of instruments, surgeons may utilize a cannula through which the instruments may be passed. The cannula can further assist in maintaining the incision in an open position to enable ready access to the incision. Thus, a surgeon may utilize a plurality of cannulas during an ophthalmic procedure to enable simultaneous or sequential utilization of multiple microsurgical instruments and/or aspiration or infusion lines.

Certain types of cannulas comprise a narrow tube with an attached hub, which may or may not be valved. Valved cannulas were developed to address the issue of fluids flowing out of the tube when the tube is not connected to an infusion device, or when an instrument is not inserted within the tube because the interior of the eye is pressurized. To attach the cannula, the surgeon may utilize a trocar-cannula insertion tool, which comprises a handle or lance having a trocar and cannula disposed at a distal end thereof. Together, the trocar and cannula may be referred to as a trocar-cannula assembly. Utilizing the trocar-cannula insertion tool, the surgeon may make an incision on the eye (e.g., with the trocar through the sclera) and insert the tube of the cannula through the incision up to the hub, which acts as a stop that prevents the tube from entering the eye completely. Prior to making the incision, the surgeon may "mark" the incision site with a scleral marker tool, and further move or manipulate conjunctival tissue and/or debris away from the incision site with a tissue manipulator tool. Often, the scleral marker and/or tissue manipulator are separate instruments from the trocar-cannula insertion tool and/or each other, or are formed on an opposite end of the trocar-cannula insertion tool from the trocar-cannula assembly. Thus, performance of scleral marking and/or tissue manipulation requires the utilization of separate instruments, or the trocar-cannula insertion tool must be "flipped" in between using the scleral marker and/or tissue manipulator and the trocar-cannula assembly, thereby increasing the complexity of a surgical procedure and decreasing efficiency.

Therefore, there is a need for improved devices, systems, and methods for scleral marking and scleral manipulation prior to cannula insertion, and there is a particular need for improved trocar-cannula insertion tools that address the drawback described above.

SUMMARY

The present disclosure relates to surgical tools, and more specifically, to trocar-cannula insertion tools and methods of use thereof.

According to certain embodiments, a cap for an ophthalmic surgical instrument is provided. The cap includes a body having a proximal end and a distal end opposite the proximal end. A marking element extends in a distal direction from the distal end of the body and includes at least one marking tip. A manipulation element extends from the body in a direction different from the marking element and includes at least one manipulation tip.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body.

As used herein, the term "about" may refer to a +/−10% variation from the nominal value. It is to be understood that such a variation can be included in any value provided herein.

Embodiments of the present disclosure generally relate to trocar-cannula insertion tools for ophthalmic procedures. In certain embodiments, a cap for a trocar-cannula insertion tool includes a body having a proximal end and a distal end opposite the proximal end. A marking element extends in a distal direction from the distal end of the body and includes at least one marking tip for forming one or more indentations on a patient's eye during an ophthalmic procedure. A manipulation element extends from the body in a direction different from the marking element and includes at least one manipulation tip for gripping a tissue of the patient's eye during the ophthalmic procedure. In certain embodiments, the cap further includes a window for exposing a photoluminescent cannula of the trocar-cannula insertion tool to light, enabling the cannula to absorb photons prior to insertion thereof.

Figure 1:
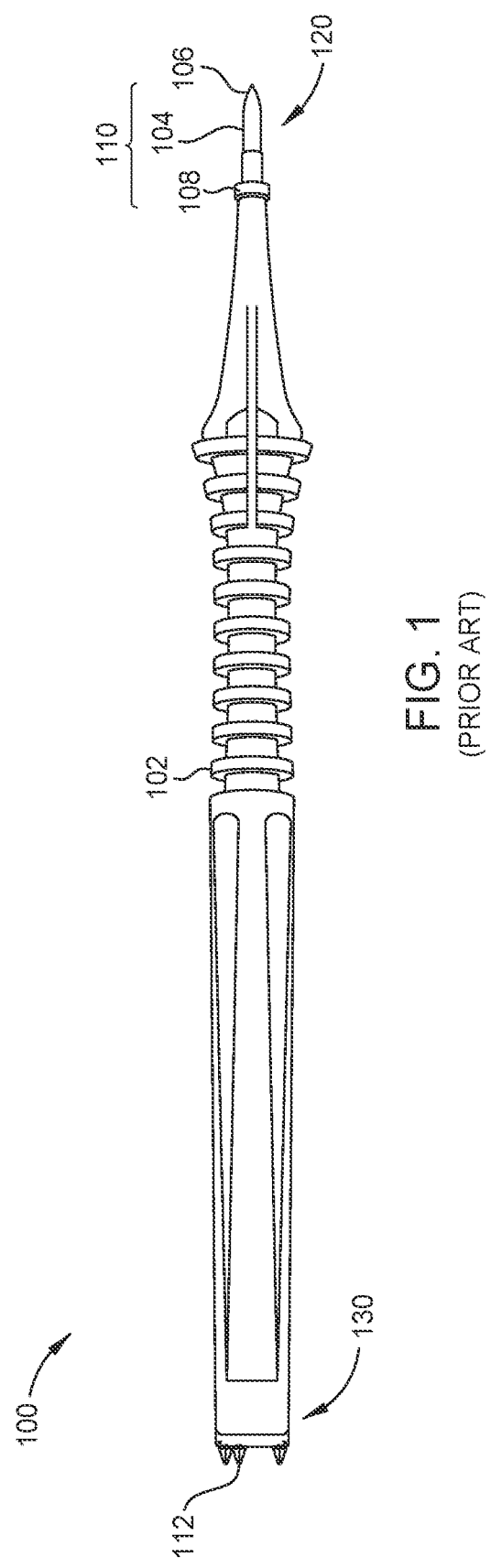
FIG. 1 illustrates a side view of a conventional trocar-cannula insertion tool, in accordance with certain embodiments of the present disclosure.

FIG. 1 illustrates a side view of a conventional ophthalmic trocar-cannula insertion tool 100 for inserting a cannula into an eye of a patient, according to certain embodiments of the present disclosure. The trocar-cannula insertion tool 100 generally includes a handle 102 having a distal end 120 and a proximal end 130. A trocar 104 having a blade 106 extends in a distal direction from the distal end 120 of the handle 102 and supports a cannula 108 thereon. Together, the trocar 104 and cannula 108 are referred to as a trocar-cannula assembly 110. The trocar 104 is fixed to the handle 102 and is configured to puncture the sclera of the patient's eye to insert the cannula 108 therein, which slides off the trocar 104 and remains in the incision site upon removal of the trocar-cannula insertion tool 100.

The trocar-cannula insertion tool 100 further includes an accessory tool 112 disposed at the proximal end 130, which may be a scleral marker and/or tissue manipulator. For example, the accessory tool 112 may be utilized by the surgeon prior to inserting the cannula 108 to mark the desired incision site on the sclera and/or displace conjunctival tissue around the incision site. Since the accessory tool 112 is disposed on the trocar-cannula insertion tool 100 along with the trocar-cannula assembly 110, the accessory tool 112 may not be utilized simultaneously with the trocar-cannula assembly 110, but rather, only in sequence therewith. Furthermore, in order to utilize both tools disposed at opposite ends 120, 130 of the trocar-cannula insertion tool 100, the surgeon must flip (e.g., rotate along a non-axial center) the trocar-cannula insertion tool 100 in between uses. Accordingly, insertion of the cannula 108 with the trocar-cannula insertion tool 100 of FIG. 1 may add increased difficulty to a surgical procedure and may be inefficient.

Figure 2A:
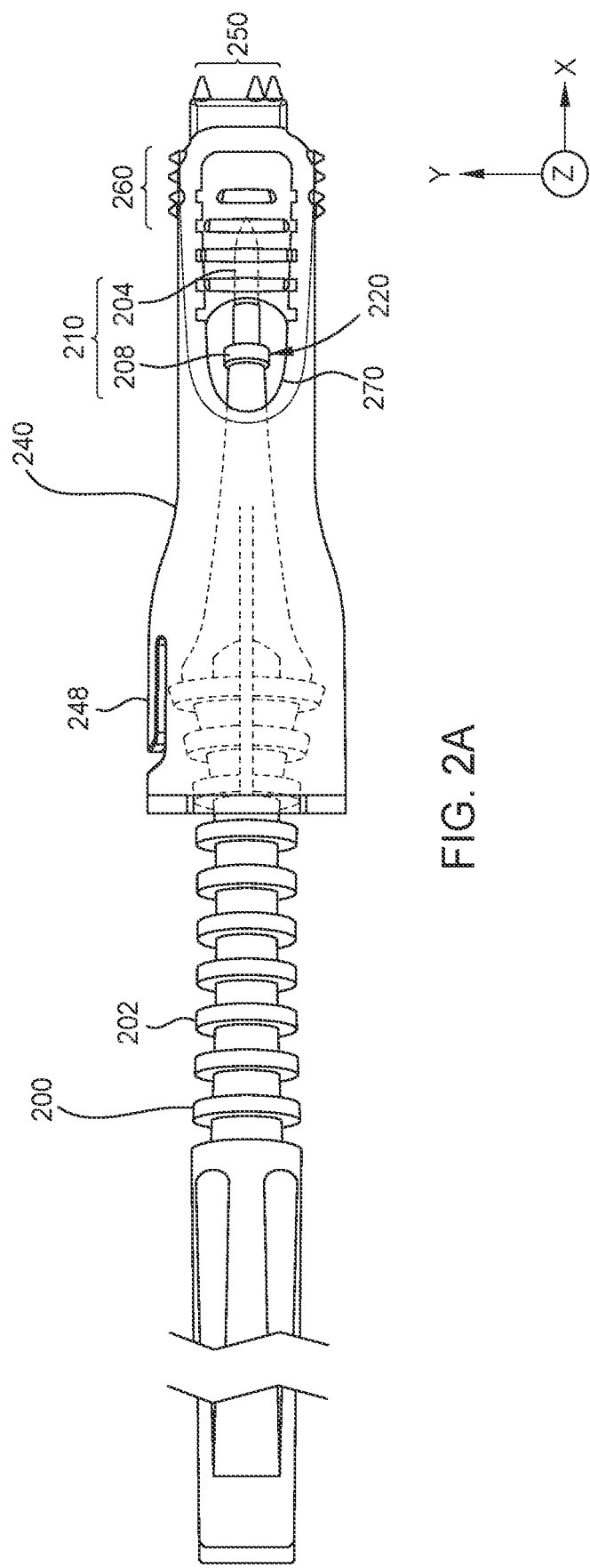
FIG. 2A illustrates a side schematic view of an exemplary cap for a trocar-cannula assembly, in accordance with certain embodiments of the present disclosure.

FIG. 2A is a schematic side view of an exemplary cap 240 for a trocar-cannula insertion tool, according to certain embodiments of the present disclosure. The cap 240 efficiently facilitates both functions of scleral marking and tissue manipulation, and thus overcomes many of the drawbacks associated with conventional trocar-cannula insertion tools having a scleral marker and/or tissue manipulator disposed on the insertion tool itself.

As shown in FIG. 2A, the cap 240 is secured over a trocar-cannula insertion tool 200, which may be substantially similar to the trocar-cannula insertion tool 100 described above. The trocar-cannula insertion tool 200 generally includes a handle 202 having a distal end 220 with a trocar-cannula assembly 210, e.g., a trocar 204 supporting a cannula 208 thereon. The cap 240 is configured to slide over the distal end 220 of the handle 202 and lock in place over the trocar-cannula assembly 210, as well as a portion of the handle 202, to protect the trocar-cannula assembly 210 and prevent undesired contact of the trocar 204 with foreign objects. The cap 240 may include one or more engagement features 248 that mate with one or more reciprocal engagement features of the trocar-cannula insertion tool 200 to secure the cap thereon.

In certain embodiments, the cannula 208 is a photoluminescent cannula that emits light (i.e., glows) upon energization for better visualization thereof in low to no-light surgical conditions. In such embodiments, the cannula 208 may require exposure to light prior to the surgical procedure, e.g., during setup, in order to energize. The cap 240 advantageously includes a window 270 formed therein at a position adjacent to the cannula 208 when the cap 240 is secured to the trocar-cannula insertion tool 200. Thus, the window 270 facilitates exposure of the cannula 208 to light while the trocar-cannula insertion tool 200 is engaged with the cap 240, effectively enabling the photoluminescent cannula 208 to energize or "charge" in pocket before being inserted into the patient's eye.

The cap 240 further includes a marking element 250 and a manipulation element 260 formed thereon, which may each include one or more features for scleral marking or tissue manipulation, respectively. During operation, a user, such as a surgeon, may remove the cap 240 with one hand and use either of the marking element 250 or the manipulation element 260 while holding the trocar-cannula insertion tool 200 with the other hand. The inclusion of both the marking element 250 and the manipulation element 260 on the cap 240, rather than on the trocar-cannula insertion tool 200, enables the surgeon, to mark the sclera of the patient's eye and/or displace the conjunctiva thereof while inserting the trocar-cannula assembly 210 into the eye with the other hand, or shortly beforehand. Furthermore, the aforementioned actions may be completed by the surgeon without changing the relative orientation of the trocar-cannula insertion tool 200.

Figure 2B:
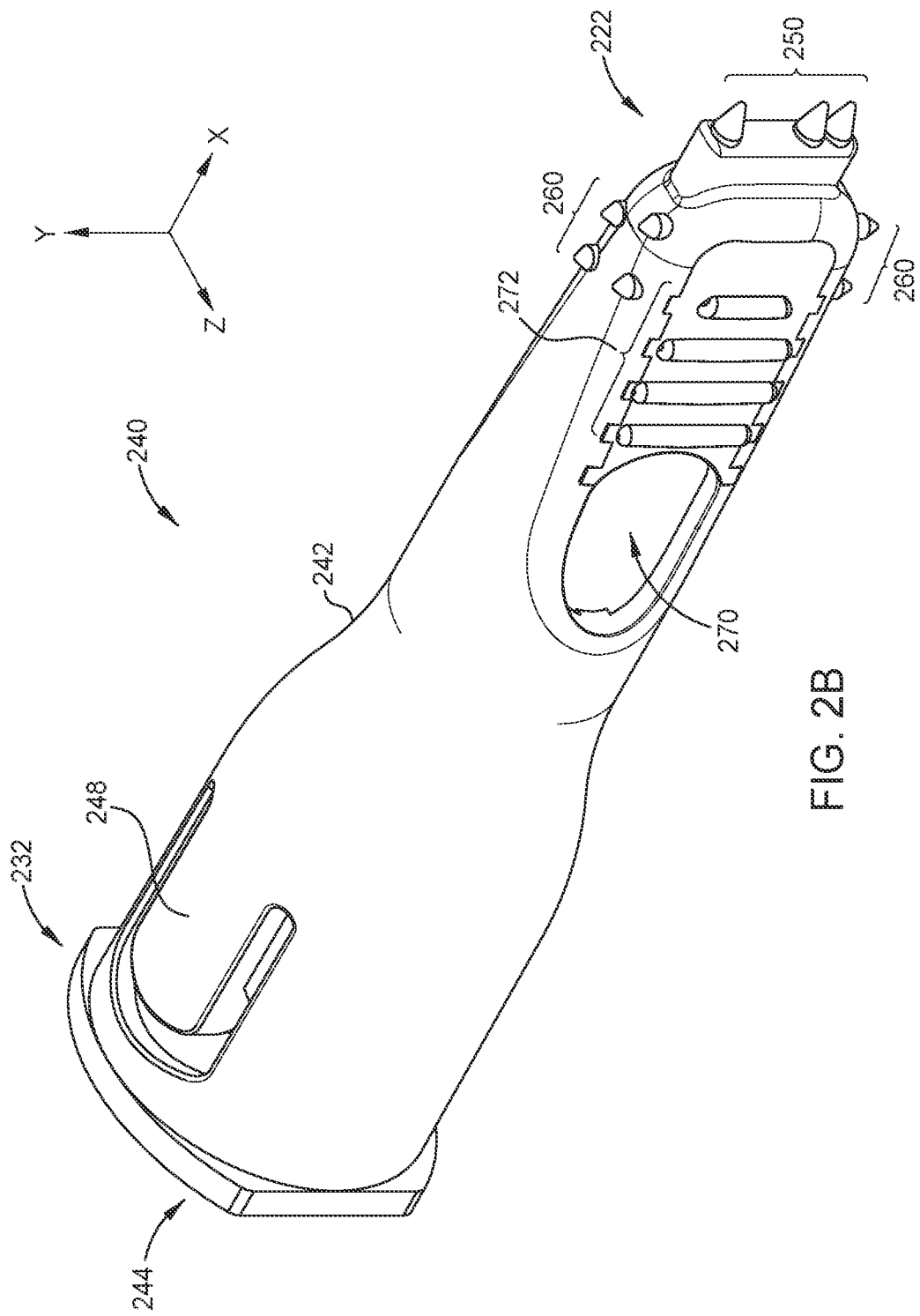
FIG. 2B illustrates an isometric view of the exemplary cap of FIG. 2A, in accordance with certain embodiments of the present disclosure.
Figure 2C:
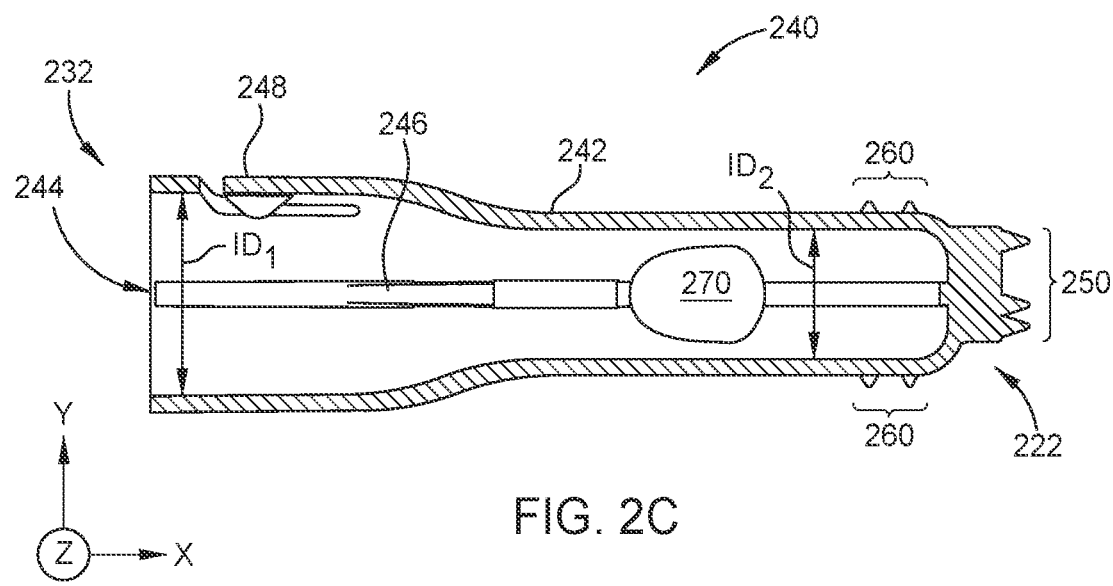
FIG. 2C illustrates a side cross-sectional view of the exemplary cap of FIG. 2A, in accordance with certain embodiments of the present disclosure.
Figure 2D:
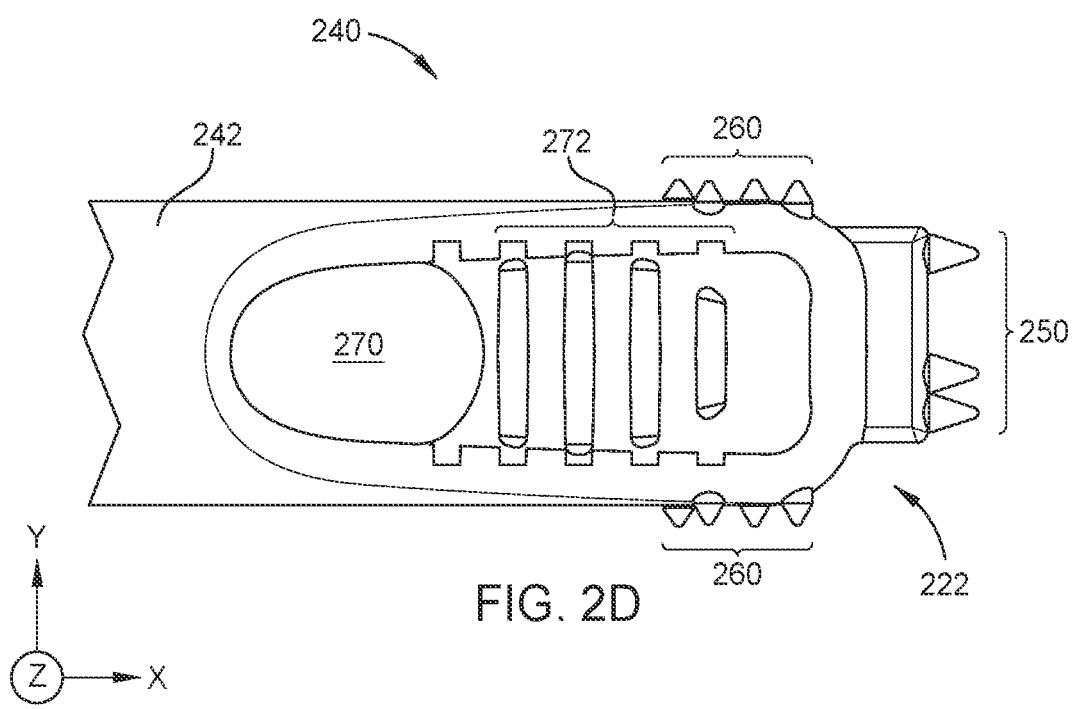
FIG. 2D illustrates an enlarged view of a portion of the exemplary cap of FIG. 2A, in accordance with certain embodiments of the present disclosure.
Figure 2E:
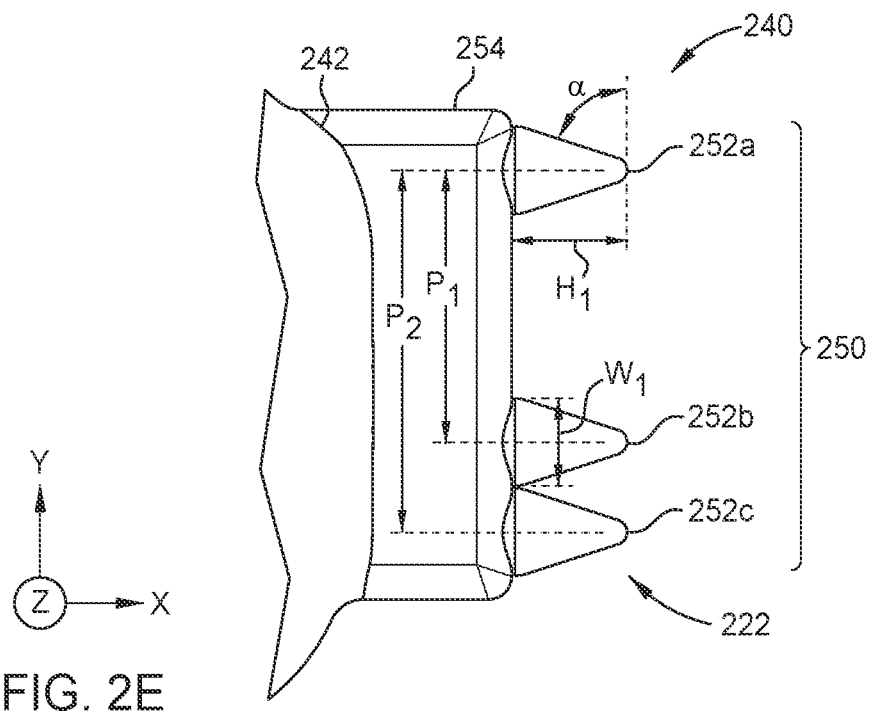
FIG. 2E illustrates an enlarged view of a portion of the exemplary cap of FIG. 2A, in accordance with certain embodiments of the present disclosure.
Figure 2F:
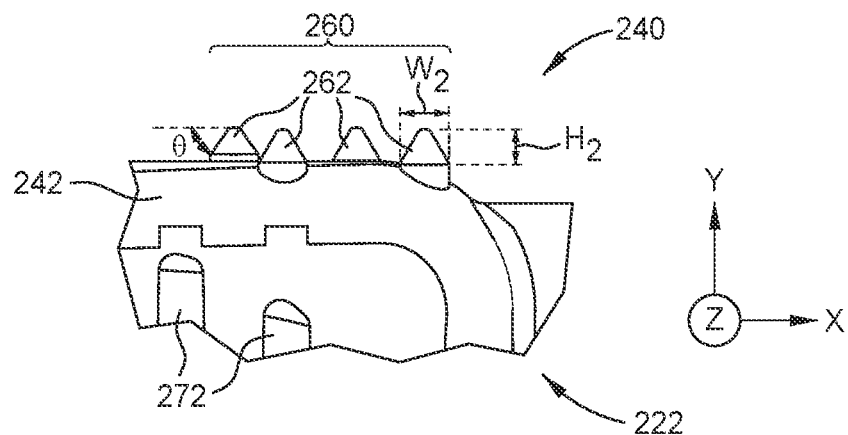
FIG. 2F illustrates an enlarged view of a portion of the exemplary cap of FIG. 2A, in accordance with certain embodiments of the present disclosure.
Figure 2G:
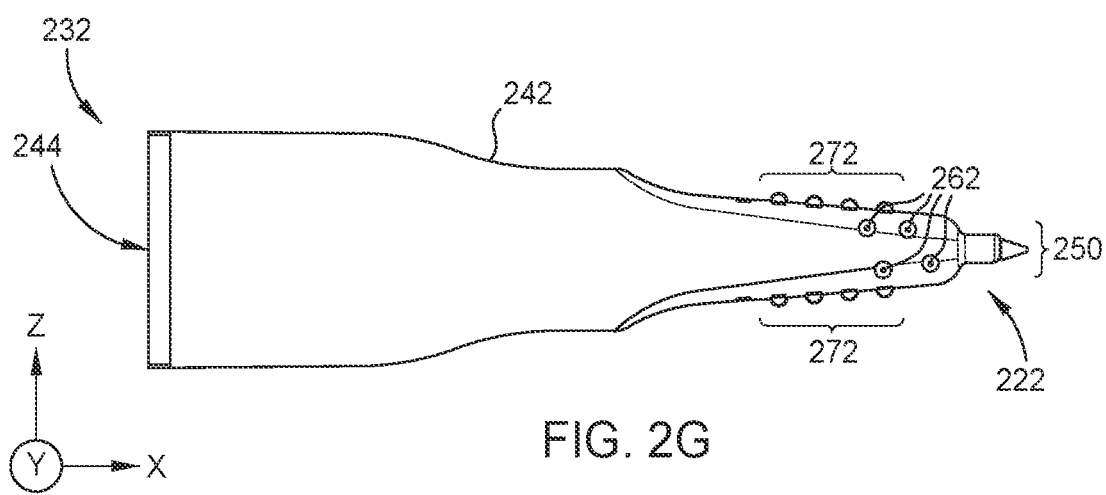
FIG. 2G illustrates an alternative side view of the exemplary cap of FIG. 2A, in accordance with certain embodiments of the present disclosure.

FIGS. 2B-2G include additional views of the cap 240 of FIG. 2A. FIG. 2B is an isometric view of the cap 240; FIG. 2C is a side cross-sectional view of the cap 240; FIGS. 2D-2E are enlarged partial views of the cap 240; FIG. 2F is a side cross-sectional view of the cap 240; and FIG. 2G is an alternative side view of the cap 240. FIGS. 2A-2G are, therefore, herein described together herein for clarity.

The cap 240 generally includes a hollow and ergonomically shaped body 242 having an opening 244 disposed at a proximal end 232 thereof for receiving a trocar-cannula insertion tool, such as the trocar-cannula insertion tool 200. An inner morphology of the body 242 is shaped to closely receive (e.g., with little tolerance) the trocar-cannula insertion tool 200 and enable the cap 240 to securely rest thereon. Thus, in certain embodiments, the body 242 has a variable inner dimension (e.g., diameter or width) along a major axis X of the cap 240 that substantially conforms to the outer dimensions of the trocar-cannula insertion tool 200. For example, as shown in the cross-section in FIG. 2C, the body 242 includes at least a first inner dimension $ID_1$ adjacent the proximal end 232 that transitions into a second inner dimension $ID_2$ adjacent a distal end 222 of the body 242, enabling the cap 240 to closely receive both the handle 202 and the trocar-cannula assembly 210 of the trocar-cannula insertion tool 200. The transition between the first inner dimension $ID_1$ and the second inner dimension $ID_2$ may be step-wise or curvilinear. In certain embodiments, the outer morphology of the body 242 may substantially track (e.g., match) the inner morphology thereof, and thus, the body 242 may have at least a first outer dimension adjacent the proximal end 232 that transitions into a second outer dimension adjacent the distal end 222.

In certain embodiments, the body 242 includes one or more guides 246 formed on an inner wall thereof to facilitate direction of the trocar-cannula insertion tool 200 when being received and/or withdrawn from the cap 240. The one or more guides 246 may also provide additional support for the cap 240 when secured on the trocar-cannula insertion tool 200, further reducing any relative movement therebetween. As described above, the body 242 further includes one or more engagement features 248 which fasten the cap 240 on the trocar-cannula insertion tool 200 by engaging (e.g., mating) with one or more reciprocal features on the trocar-cannula insertion tool 200. In certain embodiments, the engagement features 248 include a flange, inward-facing protrusion, thread, or the like.

In certain embodiments, one or more ribs 272 extend laterally outward from an outer wall of the body 242 to facilitate improved and ergonomic gripping by the surgeon. For example, as shown in FIG. 2D, the body 242 includes a plurality of ribs 272 formed on at least one side of the cap 240 and adjacent to the distal end 222. In certain embodiments, the body 242 includes two pluralities of ribs 272 formed on opposing sides of the cap 240 and extending in substantially opposite lateral directions from the body 242.

The body 242 further includes at least one window 270 formed through a wall thereof for exposing the cannula 208 to exterior light when the cap 240 is engaged with the trocar-cannula insertion tool 200. As previously described, in certain surgical procedures, cannula 208 may be a photoluminescent cannula, such as a phosphorescent cannula, for easier visualization of the cannula in low light conditions. Thus, the formation of the window 270 in the body 242 creates a port through which light may pass to the photoluminescent cannula 208 prior to a surgical procedure, allowing the cannula 208 to energize while still being covered by the cap 240. In certain embodiments, two windows 270 are formed in the body 242 on opposing sides of the cap 240 for optimizing the amount of light passing into the interior of the cap 240. Generally, the window(s) 270 may have any suitable morphology and size. For example, the window(s) 270 may be circular, oblong, polygonal (e.g., regular or irregular), ovoid, or the like.

In certain embodiments, the marking element 250 is formed on the distal end 222 of the body 242, although other positions on the body 242 are also contemplated. As shown in FIG. 2E, the marking element 250 includes a plurality of marking tips 252 extending in a distal direction from the body 242 and formed in a linear arrangement. During use, a surgeon may remove the cap 240 from the trocar-cannula insertion tool 200 and press the marking tips 252 against the sclera of a patient's eye to form indentations thereon and "mark" desired locations of incisions sites for cannula insertion.

The marking tips 252 may have any suitable morphology and size. For example, the marking tips 252 may be substantially conical, frustoconical, hemispherical, cylindrical, pyramidal, or the like. In certain examples, each marking tip 252 has a width $W_1$ (e.g., diameter) between about 0.2 inches and about 0.4 inches, such as between about 0.24 inches and about 0.38 inches. In certain examples, each marking tip 252 has a slant angle α (e.g., angle of inclination relative to plane of the marking tip base) between about 55° and about 65°, such as about 60°.

Often, incision sites for cannulas are formed at positions either about 3 mm or about 4 mm from the limbus (e.g., the border of the cornea and sclera) of the eye. Thus, in certain embodiments, the marking element 250 includes at least three marking tips 252a-c, wherein the marking tip 252b has a pitch $P_1$ of about 3 mm (millimeters) and the marking tip 252c has a pitch $P_2$ of about 4 mm, relative to the marking tip 252a, as shown in FIG. 2E. In such embodiments, when the surgeon aligns and presses the first marking tip 252a against the limbus and the other marking tips 252b-c radially outward thereof, the marking element 250 will form three indentations: a first indentation over the limbus, a second indentation spaced about 3 mm form the limbus, and a third indentation spaced about 4 mm from the limbus.

Note that, as used herein, the term "pitch" refers to the distance between central (i.e., major) axes of the referenced features. Also note that, the embodiments described above are only exemplary, and that other quantities of marking tips 252 and/or pitches disposed therebetween are further contemplated.

As illustrated in FIG. 2E, the marking element 250 may further include a base 254 formed between the body 242 and the marking tips 252. The base 254 provides better visualization of the marking tips 252 by the surgeon when marking the patient's sclera for incision, particularly when the marking element 250 is disposed on the distal end 222 of the body 242. Generally, the base 254 may have any suitable morphology and size. For example, in certain embodiments, the base 254 may have a substantially rectangular prism-like, mesa-like, or plateau-like shape with rounded ends (e.g., a stadium-like shape).

In the embodiments of FIGS. 2A-2G, the cap 240 further includes the manipulation element 260 formed adjacent to the marking element 250 on the distal end 222 of the body 242, although other positions on the body 242 are also contemplated for the manipulation element 260. The manipulation element 260 generally includes one or more manipulation tips 262, shown in FIG. 2F, for manipulating or moving various tissues of the patient's eye during a surgical procedure. For example, upon removing the cap 240 from the trocar-cannula insertion tool 200 and/or marking the patient's sclera, a surgeon may push or "comb" the manipulation tips 262 against the patient's conjunctival tissue to move the tissue with one hand, and further insert the trocar-cannula assembly 210 into the eye with the other hand simultaneously or in sequence therewith.

In certain embodiments, the manipulation element 260 includes at least one plurality of manipulation tips 262 extending from the body 242 in a lateral direction different from the one or more ribs 272. For example, the manipulation tips 262 may extend in a lateral direction oriented 90° relative to a direction of extension of the one or more ribs 272 from the body 242. In certain embodiments, the manipulation element 260 may include two pluralities of manipulation tips 262 extending in substantially opposite lateral directions from the body 242 on opposing sides of the cap 240. In each plurality, the manipulation elements 260 may be formed in any suitable arrangement, such as a linear arrangement, or a staggered arrangement as shown in FIG. 2G.

Similar to the marking tips 252, the manipulation tips 262 may have any suitable morphology and size. In certain embodiments, the manipulation tips 262 have a morphology (e.g., shape, slant angle) and/or size substantially similar to the marking tips 252. For example, the manipulation tips 262 may be substantially conical, frustoconical, hemispherical, cylindrical, pyramidal, or the like. In certain other embodiments, the manipulation tips 262 are different in size and shape from the marking tips 252. Generally, each manipulation tip 262 has a width $W_2$ (e.g., diameter) between about 0.3 inches and about 0.5 inches, such as between about 0.35 inches and about 0.45 inches, such as about 0.38 inches. In certain examples, each manipulation tip 262 has a slant angle $\Theta$ (e.g., angle of inclination relative to plane of the marking tip base) between about 65° and about 80°, such as between about 70° and about 75°, such as about 72°.

Figure 3A:
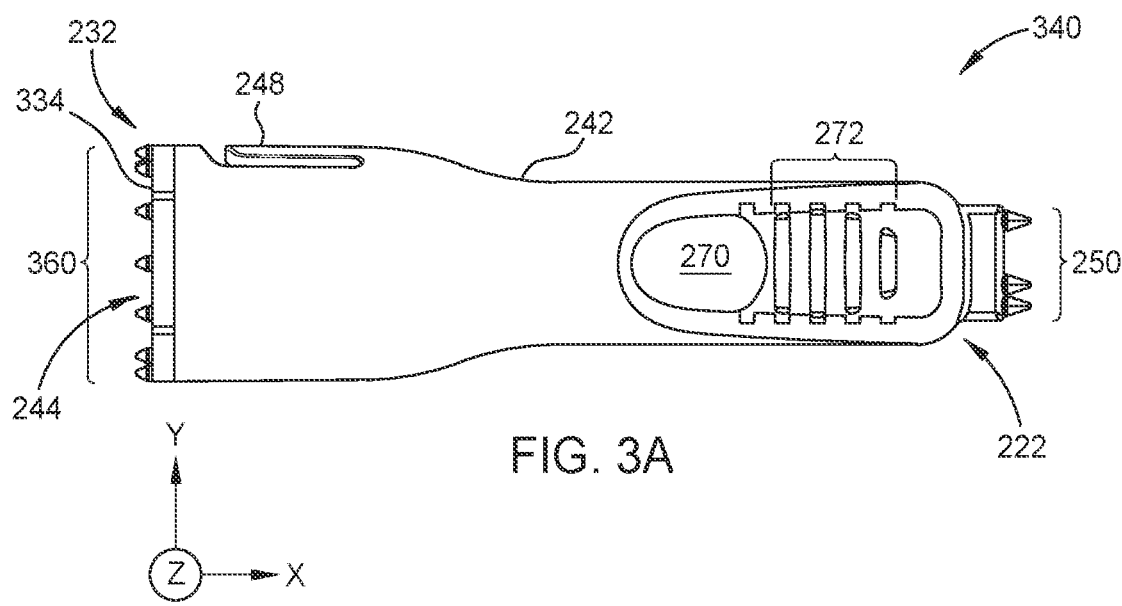
FIG. 3A illustrates a side view of another exemplary cap for a trocar-cannula assembly, in accordance with certain embodiments of the present disclosure.
Figure 3B:
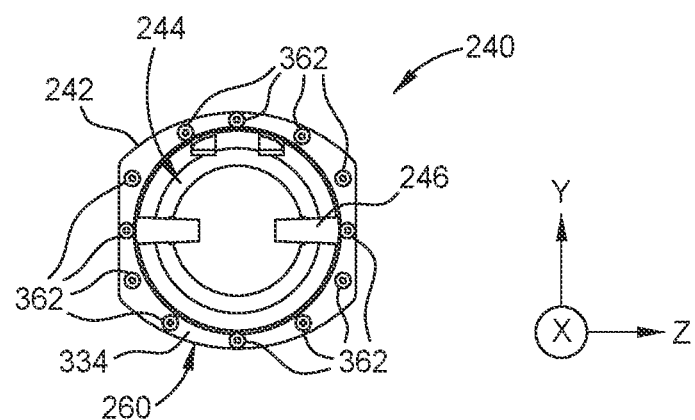
FIG. 3B illustrates an axial view of the exemplary cap of FIG. 3A, in accordance with certain embodiments of the present disclosure.

FIGS. 3A-3B are a side view and an axial view of an alternative exemplary cap 340 for a trocar-cannula insertion tool, according to certain embodiments of the present disclosure. The cap 340 is substantially similar to the cap 240, and enables efficient scleral marking and tissue manipulation during a surgical procedure.

Generally, the cap 340 includes every feature of the cap 240 described above. However, rather than having a manipulation element formed at the distal end 222 thereof and adjacent to the marking element 250, the cap 340 includes a manipulation element 360 disposed on the proximal end 232 and extending in a proximal direction therefrom. As shown in FIGS. 3A-3B, the manipulation element 360 includes one or more manipulation tips 362 formed on a proximal endface 334, which surrounds the opening 244 through which the trocar-cannula insertion tool 200 is inserted and/or removed. In certain embodiments, the manipulation element 360 includes a plurality of manipulation tips 362 formed around the opening 244, and the manipulation tips 362 may partially or completely encircle the opening 244. During use, the surgeon may use the cap 340 in substantially the same manner as the cap 240, but for having to rotate the cap 340 in between using the marking element 250 and manipulation element 360. Thus, the surgeon may mark the patient's sclera and/or manipulate the patient's conjunctival tissue with one hand, while simultaneously or sequentially inserting a trocar-cannula assembly into the patient's eye with the other hand.

In summary, embodiments of the present disclosure generally relate to trocar-cannula insertion tools for ophthalmic procedures. In particular, the embodiments herein provide an improved ergonomic cap for a trocar-cannula insertion tool which combines the functions of scleral marking and tissue manipulation, thus enabling a user to perform scleral marking and/or tissue manipulation with one hand, while inserting a cannula into the patient's eye with the other hand. Even further, the cap includes a window formed therein to facilitate the passing of light towards a photoluminescent cannula supported by the trocar-cannula insertion tool, thus enabling the excitation of the cannula prior to uncapping and insertion thereof. Accordingly, the described embodiments enable more efficient cannula insertion as compared to conventional tools and devices.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

Example Embodiments

Embodiment 1: A method of inserting a cannula into an eye of a patient, comprising: pressing a marking element of a first device into a sclera of the patient's eye to form one or more indentations on the sclera; combing a manipulation element of the first device across a conjunctival tissue of the patient's eye to move the conjunctival tissue, wherein the manipulating element is different from the marking element, and wherein the pressing of the marking element and the combing of the manipulating element are performed with a first hand; and, inserting the cannula into the patient's eye at one of the one or more indentations on the sclera, wherein the inserting of the cannula is carried out with a second hand.

Embodiment 2: The method of Embodiment 1 described above, wherein the inserting the cannula is performed simultaneously with the combing of the manipulating element.

What is claimed is:

1. A removable cap for an ophthalmic surgical instrument, comprising:
   a body comprising a proximal end and a distal end opposite the proximal end; and
   a marking element extending in a first direction from the distal end of the body, the marking element comprising at least one marking tip;
   wherein the removable cap is configured to slide over a distal end of a trocar insertion tool that comprises a handle and a trocar extending from the handle for supporting a cannula thereon;
   wherein the removable cap comprises an engagement feature that mates with a reciprocal engagement feature on the trocar insertion tool; and
   wherein the removable cap is configured to be removed completely from the trocar insertion tool before the trocar insertion tool is used to puncture a sclera of an eye to insert the cannula therein.

2. The removable cap of claim 1, wherein the marking element is configured to form one or more indentations on a patient's eye upon pressing the marking element thereagainst.

3. The removable cap of claim 1, wherein the at least one marking tip comprises three marking tips disposed in a linear arrangement.

4. The removable cap of claim 3, wherein a pitch between a first marking tip of the three marking tips and an adjacent second marking tip of the three marking tips is different from a pitch between the second marking tip and a third marking tip of the three marking tips.

5. The removable cap of claim 1, wherein the marking element further includes a mesa disposed between the body and the at least one marking tip.

6. The removable cap of claim 1, further comprising:
   a manipulation element extending from the body in a second direction different from the first direction, the manipulation element comprising at least one manipulation tip.

7. The removable cap of claim 6, wherein the manipulation element is configured to move a tissue of a patient's eye upon pressing the manipulation element thereagainst.

8. The removable cap of claim 7, wherein the second direction is oriented opposite the first direction.

9. The removable cap of claim 7, wherein the manipulation element extends in a lateral direction from an area of the body adjacent the marking element.

10. The removable cap of claim 6, wherein the at least one manipulation tip comprises a plurality of manipulation tips surrounding an opening of the body, the opening for receiving the ophthalmic surgical instrument.

11. The removable cap of claim 6, wherein the at least one manipulation tip comprises a plurality of manipulation tips disposed in a staggered arrangement.

12. The removable cap of claim 6, wherein the at least one manipulation tip comprises a first manipulation tip extending in a first lateral direction and a second manipulation tip extending in a second lateral direction different than the first lateral direction.

13. The removable cap of claim 1, further comprising one or more ribs formed in the body proximate the distal end and configured to be held by a user.

14. The removable cap of claim 1, further comprising at least one window formed in the body, the window exposing a portion of the surgical instrument when the surgical instrument is engaged with the removable cap.

15. The removable cap of claim 14, wherein the at least one window comprises two windows formed in opposing walls of the body.

* * * * *